(12) United States Patent
Gardner et al.

(10) Patent No.: US 8,709,387 B2
(45) Date of Patent: Apr. 29, 2014

(54) THERAPEUTIC VITAMIN D SUN-PROTECTING FORMULATIONS AND METHODS FOR THEIR USE

(71) Applicants: Margaret M. Gardner, Gladwyne, PA (US); Charles L. Pamplin, III, Chapel Hill, NC (US)

(72) Inventors: Margaret M. Gardner, Gladwyne, PA (US); Charles L. Pamplin, III, Chapel Hill, NC (US)

(73) Assignee: Avidas Pharmaceuticals LLC, Doylestown, PA (US)

( * ) Notice: Subject to any disclaimer, the term of this patent is extended or adjusted under 35 U.S.C. 154(b) by 0 days.

(21) Appl. No.: 13/892,831

(22) Filed: May 13, 2013

(65) Prior Publication Data

US 2013/0344014 A1   Dec. 26, 2013

Related U.S. Application Data

(62) Division of application No. 12/535,660, filed on Aug. 4, 2009, now Pat. No. 8,470,304.

(51) Int. Cl.
*A61K 8/34* (2006.01)
*A61Q 17/04* (2006.01)

(52) U.S. Cl.
USPC ............................................. 424/60; 424/59

(58) Field of Classification Search
USPC ............ 424/59, 60, 78.04, 450, 489; 514/912
See application file for complete search history.

(56) References Cited

U.S. PATENT DOCUMENTS

| | | | |
|---|---|---|---|
| 3,981,996 A | 9/1976 | Leigh | |
| 4,230,701 A | 10/1980 | Holick | |
| 4,310,511 A | 1/1982 | Holick | |
| 4,335,120 A | 6/1982 | Holick | |
| 4,847,069 A | 7/1989 | Bissett | |
| 4,847,071 A | 7/1989 | Bissett | |
| 4,847,072 A | 7/1989 | Bissett | |
| 4,869,897 A | 9/1989 | Chatterjee | |
| RE33,107 E | 11/1989 | Dikstein | |
| 4,946,671 A | 8/1990 | Bissett | |
| 4,954,332 A | 9/1990 | Bissett | |
| 5,039,513 A | 8/1991 | Chatterjee | |
| 5,039,516 A | 8/1991 | Goodman | |
| 5,167,953 A | 12/1992 | Holick | |
| 5,194,248 A | 3/1993 | Holick | |
| 5,306,485 A | 4/1994 | Robinson | |
| 5,384,115 A | 1/1995 | Bissett | |
| 5,395,829 A | 3/1995 | Holick | |
| 5,422,099 A | 6/1995 | Holick | |
| 5,487,884 A | 1/1996 | Bissett | |
| 5,532,229 A * | 7/1996 | Vieth | 514/168 |
| 5,629,021 A | 5/1997 | Wright | |
| 5,662,957 A | 9/1997 | Wright | |
| 5,700,451 A | 12/1997 | Yue | |
| 5,709,847 A | 1/1998 | Bissett | |
| 5,728,371 A | 3/1998 | Pinzon | |
| 5,728,372 A | 3/1998 | Pinzon | |
| 5,747,049 A | 5/1998 | Tominaga | |
| 5,811,414 A | 9/1998 | Bryce | |
| 5,952,317 A | 9/1999 | Deluca | |
| 5,968,485 A | 10/1999 | Robinson | |
| 5,972,316 A | 10/1999 | Robinson | |
| 5,976,513 A | 11/1999 | Robinson | |
| 6,187,763 B1 | 2/2001 | Mochizuki | |
| 6,217,852 B1 | 4/2001 | Gildenberg | |
| 6,284,234 B1 | 9/2001 | Niemiec | |
| 6,419,913 B1 | 7/2002 | Niemiec | |
| 6,440,402 B1 | 8/2002 | Gonzalez | |
| 6,599,513 B2 | 7/2003 | Deckers | |
| 6,632,671 B2 | 10/2003 | Unger | |
| 6,689,922 B1 | 2/2004 | Bernardon | |
| 6,706,725 B1 | 3/2004 | Bernardon | |
| 6,720,001 B2 | 4/2004 | Chen | |
| 6,831,106 B1 | 12/2004 | Bernardon | |
| 6,878,693 B2 | 4/2005 | Goldshtein | |
| 6,958,148 B1 | 10/2005 | Green | |
| 7,001,592 B1 | 2/2006 | Traynor | |
| 7,025,952 B1 | 4/2006 | Traynor | |
| 7,081,450 B2 | 7/2006 | Goldshtein | |
| 7,115,287 B2 | 10/2006 | Froggatt | |
| 7,128,900 B2 | 10/2006 | Buchholz | |
| 7,198,801 B2 | 4/2007 | Carrara | |
| 7,226,582 B2 | 6/2007 | Traynor | |
| 7,264,795 B2 | 9/2007 | Pflucker | |
| 7,371,738 B2 | 5/2008 | Mohapatra | |
| 7,374,779 B2 | 5/2008 | Chen | |
| 7,404,965 B2 | 7/2008 | Carrara | |

(Continued)

FOREIGN PATENT DOCUMENTS

WO   WO2011/017380 A1   2/2011
WO   WO2013003803 A1   1/2013

OTHER PUBLICATIONS

"Facts and statistics about osteoporosis and its impact." International Osteoporosis Foundation. http://www.iofbonehealth.org/facts-and-statistics.html, (2011).

(Continued)

*Primary Examiner* — Anoop Singh
*Assistant Examiner* — Anna Falkowitz
(74) *Attorney, Agent, or Firm* — Lange IP Law

(57) ABSTRACT

The present invention concerns topical sun-protecting formulations including therapeutically effective amounts of Vitamin D, including formulations that provide Vitamin D in bioavailable amounts that correspond to decreased natural Vitamin D production resulting from the sun-blocking effects of the formulations and formulations for the prevention and treatment of disorders and disease states associated with vitamin D deficiency and vitamin D insufficiency.

24 Claims, No Drawings

(56) References Cited

U.S. PATENT DOCUMENTS

| | | |
|---|---|---|
| 7,425,340 B2 | 9/2008 | Grenier |
| 7,470,433 B2 | 12/2008 | Carrara |
| 2001/0002397 A1 | 5/2001 | Bishop |
| 2002/0064508 A1 | 5/2002 | Lyles |
| 2003/0044437 A1 | 3/2003 | Motley |
| 2003/0119795 A1 | 6/2003 | Henner |
| 2003/0138503 A1 | 7/2003 | Staniforth |
| 2003/0220308 A1 | 11/2003 | Holick |
| 2004/0126339 A1 | 7/2004 | Roszell |
| 2004/0146539 A1 | 7/2004 | Gupta |
| 2004/0170582 A1 | 9/2004 | Harivel |
| 2004/0175335 A1 | 9/2004 | Pflucker |
| 2004/0224929 A1 | 11/2004 | Bernardon |
| 2006/0034779 A1 | 2/2006 | Arkin |
| 2006/0073107 A1 | 4/2006 | Person |
| 2006/0110415 A1 | 5/2006 | Gupta |
| 2006/0141014 A1 | 6/2006 | Eknoian |
| 2006/0188458 A1 | 8/2006 | Traynor |
| 2006/0292255 A1 | 12/2006 | Moffett |
| 2007/0059259 A1 | 3/2007 | Tierney |
| 2007/0085063 A1 | 4/2007 | Capelli |
| 2007/0224138 A1 | 9/2007 | Gibbons |
| 2007/0274932 A1 | 11/2007 | Suginaka |
| 2007/0297996 A1 | 12/2007 | Tanner |
| 2008/0112904 A1 | 5/2008 | Traynor |
| 2008/0113031 A1 | 5/2008 | Moodley |
| 2008/0221071 A1 | 9/2008 | Holick |
| 2010/0305209 A1 | 12/2010 | Theberge |
| 2011/0033399 A1 | 2/2011 | Gardner |

OTHER PUBLICATIONS

Bandeira et al., "Vitamin D Deficiency: A Global Perspective." *Arq. Bras. Endocrinol. Metab.* (2006) 50(4):640-646.

Benson, "Assessment and clinical implications of absorption of sunscreens across skin." *American journal of clinical dermatology* (2000) 217-224, 1(4).

Burnett et al., "Current sunscreen controversies: a critical review." *Photodermatology, photoimmunology & photomedicine* (2011) 58-67, 27(2).

Crew et al., "High Prevalence of Vitamin D Deficiency Despite Supplementation in Premenopausal Women With Cancer Undergoing Adjuvant Chemotherapy." *Journal of Clinical Oncology* (2009) 27(13):2151-2156.

Hall et al., "Vitamin D Deficiency in Cystic Fibrosis." *Int. J. Endocrinol.* (2010) Article ID 218691, 9 pages, doi:10.1155/2010/218691.

PCT/US2010/44319 International Search Report, Gardner, Sep. 2, 2010.

PCT/US2012/45095 International Search Report, Wright, Sep. 27, 2012.

Holick, The Vitamin D Epidemic and Its Health Consequences. *The Journal of Nutrition.* Nov. 1, 2005. vol. 135, No. 11, pp. 2739S-2748S.

Holick, "Vitamin D deficiency." *N. Engl. J. Med.* (2007) 266-281, 357(3).

Janjua et al., "Systemic absorption of the sunscreens benzophenone-3, octyl-methoxycinnamate, and 3-(4-methyl-benzylidene) camphor after whole-body topical application and reproductive hormone levels in humans." *The Journal of investigative dermatology* (2004) 57-61, 123(1).

Jiang et al., "Absorption of sunscreens across human skin: an evaluation of commercial products for children and adults." *British journal of clinical pharmacology* (1999) 635-637, 48(4).

Rosen, "Clinical practice. Vitamin D insufficiency." *N. Engl. J. Med.* (2011) 248-254, 364(3).

\* cited by examiner

THERAPEUTIC VITAMIN D SUN-PROTECTING FORMULATIONS AND METHODS FOR THEIR USE

RELATED APPLICATION DATA

This application is a continuation of, and claims priority to, U.S. patent application Ser. No. 12/535,660, filed on Aug. 4, 2009, the entirety of which is hereby incorporated by reference.

FIELD OF THE INVENTION

The present invention relates to topical sun-protecting formulations that include therapeutically effective amounts of Vitamin D for supplementing vitamin D due to decreased vitamin D production resulting from the sun-protecting component(s) of the formulations, for treating vitamin D deficient and vitamin D insufficient mammals, and for preventing and treating disorders and diseases associated with vitamin D deficiency and vitamin D insufficiency.

BACKGROUND OF RELATED TECHNOLOGY

Vitamin D is a fat-soluble vitamin that is essential to a number of biological processes, including promoting calcium absorption in the gut, maintaining adequate serum calcium and phosphate concentrations (to enable normal bone mineralization and to prevent hypocalcemic tetany), and is needed for bone growth and bone remodeling by osteoblasts and osteoclasts (van den Berg, H. (1997) *Eur. J. Clin. Nutr.* 51:S76-9; Institute of Medicine, Food and Nutrition Board. (1997) *Dietary Reference Intakes: Calcium, Phosphorus, Magnesium, Vitamin D, and Fluoride.* Washington, DC: National Academy Press; Cranney C. et al. (2007) Evidence Report/Technology Assessment No. 158 prepared by the University of Ottawa Evidence-based Practice Center under Contract No. 290-02.0021. *AHRQ Publication No.* 07-E013. Rockville, Md.: Agency for Healthcare Research and Quality). Insufficient vitamin D may result in thin, brittle, and/or misshapen bones, and is a cause of rickets in children and osteomalacia in adults (DeLuca H. F. (2004) *Am. J. Clin. Nutr.* 80:1689S-96S; Goldring et al. (1995) *Endocrinology.* 3rd ed. Philadelphia: W B Saunders, 1204-27; Favus M. J. and Christakos S. (1996) *Primer on the Metabolic Bone Diseases and Disorders of Mineral Metabolism.* 3rd ed. Philadelphia, Pa.: Lippincott-Raven). Together with calcium, vitamin D also helps protect older adults from osteoporosis.

Vitamin D also has other roles in human health, including modulation of neuromuscular and immune function and reduction of inflammation. Many genes encoding proteins that regulate cell proliferation, differentiation, and apoptosis are modulated in part by vitamin D (van den Berg (1999); Cranney et al. (2007); Holick, M. F. (2003) *Cancer Res.* 164:3-28; Hayes et al. (2003) Cell. Mol. Biol. 49:277-300). Vitamin D deficiency has been linked to breast, prostate and colon cancer, as well as autoimmune diseases such as multiple sclerosis, fibromyalgia, rheumatoid arthritis, Grave's disease, lupus, and others. High serum vitamin $D_3$ levels have also been linked to a reduced risk for skin cancers (See Roehr. B. *Dermatology Times.* July 2009, p. 24)

Vitamin D is naturally produced when the skin is exposed to adequate sunlight, specifically when ultraviolet B (UVB) radiation is strong enough to penetrate the epidermal layers of the skin. Factors that impact the strength UVB radiation, including time of year, latitude, altitude, cloud cover, and pollution, may therefore likewise affect the natural production of vitamin D. For example, complete cloud cover has been shown to reduces UV energy levels by 50% and shade (including that produced by severe pollution) has been shown to reduce UV energy levels by 60% (Wharton B. and Bishop N. (2003) *Lancet.* 362:1389-400). As vitamin D is naturally present in very few foods, sufficient UVB exposure and/or supplementation is important to maintaining proper Vitamin D levels.

Although sun exposure is critical to natural vitamin D synthesis, UV radiation is a carcinogen responsible for most of the estimated 1.5 million skin cancers and the 8,000 deaths due to metastatic melanoma that occur annually in the United States (Wharton and Bishop, 2003), and lifetime cumulative UV damage to skin is also largely responsible for age-associated dryness and other cosmetic changes. Protecting the skin from the harmful effects of ultraviolet A (UVA) and UVB radiation is therefore critical for reducing the risk of skin cancers and metastatic melanoma, and therefore The American Academy of Dermatology advises that photoprotective measures be taken, including the use of sunscreen, whenever an individual is exposed to the sun (American Academy of Dermatology. *Position statement on vitamin D.* Nov. 1, 2008). However, sunscreens with a sun protection factor of 8 or more have been shown to block vitamin D producing UV rays, and may therefore interfere with the natural production of vitamin D (Wolpowitz D. and Gilchrest B. A. (2006) *J. Am. Acad. Dermatol.* 54:301-17).

Various formulations and methods have been developed to treat vitamin D deficient individuals and/or enhance the ability of individuals to produce vitamin D, including vitamin D precursor-based formulations that are applied to the skin and irradiated to cause vitamin D synthesis, as well as topically administered formulations for increasing systemic vitamin D levels. Sunscreen formulations that incorporate vitamins (including vitamin D) for their well-known antioxidant properties are also known in the art. However, sun-protecting formulations incorporating vitamin D in therapeutically effective amounts to achieve and/or maintain adequate systemic vitamin D levels necessary for proper biological functioning, and in particular sun-protecting formulations that provide vitamin D in specific therapeutic amounts that correlate to decreased natural vitamin D production due to the sun-blocking effects of such formulations, are not known. It is therefore objects of the present invention to provide such formulations, and methods of preventing and treating disorders and diseases using such formulations.

SUMMARY OF THE INVENTION

Generally speaking, the present invention addresses certain problems and needs in the art by providing topical sun-protecting formulations that include therapeutically effective amounts of vitamin D for supplementing vitamin D due to decreased vitamin D production resulting from the sun-protecting component(s) of the formulations, for treating vitamin D deficient and vitamin D insufficient mammals, and for preventing and treating disorders and diseases associated with vitamin D deficiency and vitamin D insufficiency.

In certain non-limiting embodiments, the present invention is directed to therapeutic sun-protecting compositions including (a) at least one sun-protecting agent; (b) at least one vitamin D compound present in a therapeutically effective amount to increase serum vitamin D levels when administered to a mammal; and (c) a pharmaceutical carrier effective for topical administration of the at least one sun-protecting agent and the at least one vitamin D compound.

In certain other non-limiting embodiments, the present invention is directed to methods of preventing disorders and diseases associated with vitamin D deficiency or vitamin D insufficiency, including topically administering to a mammal a sun-protecting composition, the sun-protecting composition including: (a) at least one sun-protecting agent; (b) at least one vitamin D compound present in a therapeutically effective amount to increase serum vitamin D levels when administered to a mammal; and (c) a pharmaceutical carrier effective for topical administration of the at least one sun-protecting agent and the at least one vitamin D compound to a mammal.

In certain other non-limiting embodiments, the present invention is directed to methods of treating disorders and diseases associated with vitamin D deficiency or vitamin D insufficiency, including topically administering to a mammal having at least one disorder or disease associated with vitamin D deficiency a sun-protecting composition, the sun-protecting compositions including: (a) at least one sun-protecting agent; (b) at least one vitamin D compound present in a therapeutically effective amount to increase serum vitamin D levels when administered to a mammal; and (c) a pharmaceutical carrier effective for topical administration of the at least one sun-protecting agent and the at least one vitamin D compound to a mammal.

In certain non-limiting embodiments of the present invention, the at least one vitamin D compound in any embodiment of the present invention may be present in an amount to compensate for a reduction in a mammal's natural vitamin D production due to decreased sun exposure resulting from the at least one sun-protecting agent.

In certain non-limiting embodiments of the present invention, a mammal in any embodiment of the present invention may have a vitamin D deficiency or may have a vitamin D insufficiency.

In certain non-limiting embodiments of the present invention, a mammal in any embodiment of the present invention may have a serum (25-hydroxy) vitamin D concentration of less than about 20 ng/mL.

In certain non-limiting embodiments of the present invention, a mammal in any embodiment of the present invention may have a serum (25-hydroxy) vitamin D concentration of less than about 8 ng/mL.

In certain non-limiting embodiments of the present invention, administration of the at least one vitamin D compound to a mammal in any embodiment of the present invention may result in a serum (25-hydroxy) vitamin D concentration in such mammal in a range of about 20 ng/mL to about 100 ng/mL.

In certain non-limiting embodiments of the present invention, administration of the at least one vitamin D compound to a mammal in any embodiment of the present invention may result in a serum (25-hydroxy) vitamin D concentration in such mammal in a range of about 30 ng/mL to about 60 ng/mL.

In certain non-limiting embodiments of the present invention, the at least one vitamin D compound may be present in the compositions in any embodiment of the present invention at a concentration that results in administration of the vitamin D compound to the skin at a concentration of about 0.1 $IU/cm^2$ to about 1000 $IU/cm^2$.

In certain non-limiting embodiments of the present invention, the at least one vitamin D compound may be present in the compositions in any embodiment of the present invention at a concentration that results in administration of the vitamin D compound to the skin at a concentration of about 0.1 $IU/cm^2$ to about 10.0 $IU/cm^2$ In certain non-limiting embodiments of the present invention, a mammal in any embodiment of the present invention may have at least one disorder or disease state associated with vitamin D deficiency or vitamin D insufficiency.

In certain non-limiting embodiments of the present invention, the at least one disorder or disease state associated with vitamin D deficiency or vitamin D insufficiency in any embodiment of the present invention may be selected from the group consisting of disorders and diseases associated with low calcium uptake, bone-related disorders and diseases, vascular disorders and diseases, autoimmune disorders and diseases, tuberculosis, periodontal disease, chronic pain, seasonal affective disorder, cognitive impairment, depression, type I diabetes, chronic renal disease, hypoparathyroid, Parkinson's disease, and cancer.

In certain non-limiting embodiments of the present invention, the bone-related disorders and diseases in any embodiment of the present invention may be selected from the group consisting of osteopenia, osteomalacia, osteoporosis, and rickets.

In certain non-limiting embodiments of the present invention, the vascular disorders and diseases in any embodiment of the present invention may be selected from the group consisting of coronary artery disease, high blood pressure, and peripheral artery disease.

In certain non-limiting embodiments of the present invention, the autoimmune disorders and diseases in any embodiment of the present invention may be selected from the group consisting of multiple sclerosis, fibromyalgia, rheumatoid arthritis, Grave's disease, and lupus.

In certain non-limiting embodiments of the present invention, the cancer in any embodiment of the present invention may be selected from the group consisting of breast cancer, prostate cancer, colon cancer, and skin cancer.

In certain non-limiting embodiments of the present invention, the at least one sun-protecting agent in any embodiment of the present invention may be capable of absorbing and/or blocking ultraviolet radiation having a wavelength in the range of about 280 nm to about 400 nm.

In certain non-limiting embodiments of the present invention, the at least one sun-protecting agent in any embodiment of the present invention may be selected from the group consisting of aminobenzoic acid, avobenzone, benzophenone, benzophenone-3, cinnamates, cinoxate, dioxybenzone, ecamsule, ensulizole, ethylhexyl p-methoxycinnamate, homosalate, menthyl anthranilate, meradimate, octinoxate, octisalate, octocrylene, octyl dimethyl paba, octyl methoxycinnamate (OMC), octyl salicytate (OCS), oxybenzone, padimate-O, para-aminobenzoic acid (PABA), Parsol® 1789, salicylates, sulisobenzone, sulisobenzone, titanium dioxide, trolamine salicylate, and zinc oxide In certain non-limiting embodiments of the present invention, the at least one vitamin D compound in any embodiment of the present invention may be selected from the group consisting of vitamin $D_2$ (ergocalciferol), vitamin $D_3$ (cholecalciferol), vitamin D precursors, inactive forms, active forms, and metabolites thereof.

In certain non-limiting embodiments of the present invention, the at least one sun-protecting agent, the at least one vitamin D compound, and the pharmaceutical carrier in any embodiment of the present invention may be provided in combination in the form of a cream, gel, liquid, lotion, solution, spray, emulsion, aerosol, or a combination thereof.

In certain non-limiting embodiments of the present invention, the at least one vitamin D compound in any embodiment of the present invention may be encapsulated.

In certain non-limiting embodiments of the present invention, the pharmaceutically effective carrier in any embodiment of the present invention may be water or alcohol, or a mixture thereof.

In certain non-limiting embodiments of the present invention, the pharmaceutically effective carrier in any embodiment of the present invention may be an oil-free carrier.

In certain non-limiting embodiments of the present invention, the compositions in any embodiment of the present invention may further include at least one emollient, which in certain embodiments of the present invention may be selected from the group consisting of fatty esters, fatty alcohols, mineral oils, polyether siloxane copolymers, polypropylene glycol ("PPG")-15 stearyl ether, PPG-10 acetyl ether, steareth-10, oleth-8, PPG-4 lauryl ether, vitamin E acetate, PEG-7 glyceryl cocoate, lanolin, cetyl alcohol, octyl hydroxystearate, dimethicone, cetyl alcohol, octyl hydroxystearate, dimethicone, derivatives, combinations, and mixtures thereof.

In certain non-limiting embodiments of the present invention, the compositions in any embodiment of the present invention may further include at least one skin condition agent, which in certain embodiments of the present invention may be selected from the group consisting of colloidal oatmeal, olive leaf, sulfonated shale oil, elubiol, 6-(1-piperidinyl)-2,4-pyrimidinediamine-3-oxide, finasteride, ketoconazole, zinc pyrithione, coal tar, benzoyl peroxide, selenium sulfide, hydrocortisone, pramoxine hydrochloride, tricetylammonium chloride, polyquaternium 10, panthenol, panthenol triacetate, vitamin B, vitamin C, vitamin D, vitamin E, vitamin K, keratin, lysine, arginine, hydrolyzed wheat proteins, hydrolyzed silk proteins, octyl methoxycinnamate, oxybenzone, minoxidil, titanium dioxide, zinc dioxide, erthromycin, tretinoin, derivatives, combinations, and mixtures thereof.

In certain non-limiting embodiments of the present invention, the compositions in any embodiment of the present invention may further include at least one stabilizing agent, which in certain embodiments of the present invention may be selected from the group consisting of butylated hydroxy toluene (BHT), ethylene diamine tetra acetic acid (EDTA), triethanolamine (TEA), gylcerin, propylene glycol, derivatives, combinations, and mixtures thereof.

In certain non-limiting embodiments of the present invention, the compositions in any embodiment of the present invention may further include at least one humectant, which in certain embodiments of the present invention may be selected from the group consisting of a polyhydric alcohol selected from the group consisting of glycerol/glycerin, polyalkylene glycols, alkylene polyols, including butylene glycol, propylene glycol, dipropylene glycol, polypropylene glycol, and polyethylene glycol, sorbitol, hydroxypropyl sorbitol, hexylene glycol, 1,3-dibutylene glycol, 1,2,6,-hexanetriol, ethoxylated glycerol, propoxylated glycerol, derivatives, combinations, and mixtures thereof.

In certain non-limiting embodiments of the present invention, the compositions in any embodiment of the present invention may further include at least one buffering agent, which in certain embodiments of the present invention may be selected from the group consisting of citric acid, sodium citrate, derivatives, combinations, and mixtures thereof.

In certain non-limiting embodiments of the present invention, the compositions in any embodiment of the present invention may further include at least one viscosity adjusting agent, which in certain embodiments of the present invention may be selected from the group consisting of carbomer gelling agents, gum derivatives, derivatives, combinations, and mixtures thereof.

In certain non-limiting embodiments of the present invention, the compositions in any embodiment of the present invention may further include at least one preservative, which in certain embodiments of the present invention may be selected from the group consisting of methylparaben, ethylparaben, butylparaben, propylparaben, phenoxyethanol, derivatives, combinations, and mixtures thereof.

In certain non-limiting embodiments of the present invention, the compositions in any embodiment of the present invention may further include at least one chelating agent, which in certain embodiments of the present invention may be selected from the group consisting of ethylenediamine tetra acetic acid (EDTA), dihydroxyethyl glycine, tartaric acid, derivatives, combinations, and mixtures thereof.

In certain non-limiting embodiments of the present invention, the compositions in any embodiment of the present invention may further include at least one emulsifying agent, which in certain embodiments of the present invention may be selected from the group consisting of polysorbitate 80, glyceryl distearate, POE 10 stearyl ether, ceateareth 20, stearyl alcohol, ceteareth 20, cetearyl alcohol, derivatives, combinations, and mixtures thereof; and which in certain embodiments of the present invention may be an oil-free emulsifying agent.

In certain non-limiting embodiments of the present invention, the compositions in any embodiment of the present invention may include at least one conditioning agent, which in certain embodiments of the present invention may be selected from the group consisting of octyl hydroxystearate; emollients, such as cholesterol NF, petrolatum, mineral oils and esters, including isopropyl myristate, isopropyl palmitate, 1-decene polymer (hydrogenated), and $C_{12}$-$C_{15}$ alcohol benzoates, derivatives, combinations, and mixtures thereof.

In certain non-limiting embodiments of the present invention, the compositions in any embodiment of the present invention may further include at least one thickening agent, which in certain embodiments of the present invention may be selected from the group consisting of polyacrylamide, $C_{13}$-$C_{14}$ isoparafin, laureth-7, and derivatives, combinations, and mixtures thereof.

In certain non-limiting embodiments of the present invention, the compositions in any embodiment of the present invention may further include at least one antioxidant, which in certain embodiments of the present invention may be selected from the group consisting of ascorbic acid, ascorbyl palmitate, BHT, tocopheryl acetate, butylated hydroanisole (BHA), phenyl-α-naphthylamine, hydroquinone, propyl gallate, nordihydroquiaretic acid, *Garcinia Mangostana* (Mangosteen) Peel Extract, *Camellia Sinensis* (Green and White Tea) Leaf Extract, *Punica Granatum* (Pomegranate) Extract, and derivatives, combinations, and mixtures thereof.

In certain non-limiting embodiments of the present invention, the compositions in any embodiment of the present invention may further include the antioxidants *Garcinia Mangostana* (Mangosteen) Peel Extract, *Camellia Sinensis* (Green and White Tea) Leaf Extract, and *Punica Granatum* (Pomegranate) Extract together in combination.

In certain non-limiting embodiments of the present invention, the compositions in any embodiment of the present invention may further include at least one UV stabilizer.

In certain non-limiting embodiments of the present invention, the compositions in any embodiment of the present invention may further include at least one UV radiation absorber.

In certain non-limiting embodiments of the present invention, the compositions in any embodiment of the present invention may further include at least one fragrance, which in certain embodiments of the present invention may be selected from the group consisting of eucalyptus oil, camphor synthetic, peppermint oil, clove oil, lavender, chamomile, derivatives, combinations, and mixtures thereof.

In certain non-limiting embodiments of the present invention, the compositions in any embodiment of the present invention may further include at least one therapeutically active agent in addition to the at least one vitamin D compound, which in certain embodiments of the present invention may be present in an amount therapeutically effective for treating a disorder or disease state associated with vitamin D deficiency.

In certain non-limiting embodiments of the present invention, the compositions in any embodiment of the present invention may have a sun protection factor of from about 6 to about 95.

In certain non-limiting embodiments of the present invention, the compositions in any embodiment of the present invention may be topically administered to a mammal in a single application, or may be topically administered to a mammal in multiple applications.

DETAILED DESCRIPTION OF THE INVENTION

Generally speaking, and as discussed in greater detail in the illustrative and non-limiting Examples provided herein, the present invention is directed to cosmetic and pharmaceutical formulations and compositions (such terms being used interchangeably herein) that incorporate at least one sun-protecting agent with a therapeutically effective amount of vitamin D.

In certain exemplary, non-limiting embodiments, the inventive sun-protecting formulations include vitamin D in specific amounts that correlate to the decreased natural production of vitamin D in a mammal resulting from the sun-protecting component of the formulations, in order to prevent vitamin D deficiency and/or vitamin D insufficiency due to decreased sun exposure. It is understood that the inventive formulations may be administered to any mammal in which they are effective at increasing vitamin D levels in such mammal, and are particularly useful in mammals suited for transdermal drug delivery (such as humans, monkeys, pigs, and so forth). Therefore, the terms "mammal(s)," "individual(s)," and so forth as used herein are non-limiting and are to be construed broadly.

In certain exemplary, non-limiting embodiments, the invention sun-protecting formulations include vitamin D in specific therapeutic amounts for treating mammals having vitamin D deficiency or vitamin D insufficiency while reducing or eliminating the need for sun exposure.

In certain exemplary, non-limiting embodiments, the invention sun-protecting formulations include vitamin D in specific therapeutic amounts for treating mammals having vitamin D deficiency or vitamin D insufficiency while reducing or eliminating the need for sun exposure.

In certain exemplary, non-limiting embodiments, the inventive sun-protecting formulations provide vitamin D in specific therapeutic amounts for preventing and/or treating disorders and/or diseases associated with vitamin D deficiency and/or vitamin D insufficiency, for example and without limitation, disorders and/or diseases associated with low calcium uptake; bone-related disorders and/or diseases, including osteopenia, osteomalacia, osteoporosis, and rickets; vascular disorders and/or diseases, including coronary artery disease, high blood pressure, and peripheral artery disease; autoimmune disorders and/or diseases, including multiple sclerosis, fibromyalgia, rheumatoid arthritis, Grave's disease, and lupus; tuberculosis; periodontal disorders and/or diseases; chronic pain; seasonal affective disorder; cognitive impairment; depression; type I diabetes; chronic renal disease; hypoparathyroid; Parkinson's disease, and certain types of cancers, including breast cancer, prostate cancer, colon cancer, and skin cancer.

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions and usages provided herein take precedent over any dictionary or extrinsic definition. That the present invention may be more readily understood, select terms are defined herein according to their usage.

As used herein, "sun-protecting" agents include, for example and without limitation, any compound capable of blocking or reducing ultraviolet A (UVA) and/or ultraviolet B (UVB) radiation exposure to the skin. Examples of sun-protecting compounds include sunscreens (conventionally, products with a sun-protecting factor (SPF) of 2 or higher), sun-blocks (conventionally, products that physically block radiation exposure and/or have an SPF of 12 or higher), and combinations thereof. Sun-protecting agents may include chemical blocking agents (that may be absorbed by the skin and neutralize the effects of sunlight) and/or physical blocking agents (that sit on the surface of the skin and absorb or reflect sunlight away from the body).

Any known chemical sunblocking agent(s) may be provided in the inventive formulations, so long as such agent(s) are suitable for use in combination with a therapeutically effective amount of vitamin D including, for example and without limitation, aminobenzoic acid, avobenzone, benzophenone, benzophenone-3, cinnamates, cinoxate, dioxybenzone, ecamsule, ensulizole, ethylhexyl p-methoxycinnamate, homosalate, menthyl anthranilate, meradimate, octinoxate, octisalate, octocrylene, octyl dimethyl paba, octyl methoxycinnamate (OMC), octyl salicytate (OCS), oxybenzone, padimate-O, para-aminobenzoic acid (PABA), Parsol® 1789, salicylates, sulisobenzone, sulisobenzone, titanium dioxide, trolamine salicylate, and zinc oxide.

Any known physical sunblocking agent(s) may be provided in the present invention so long as such agent(s) are suitable for use in combination with a therapeutically effective amount of vitamin D including, for example and without limitation, zinc oxide and titanium dioxide.

As used herein, "vitamin D" refers, for example and without limitation, to any of known form of vitamin D, and specifically includes vitamin $D_2$ (ergocalciferol), vitamin $D_3$ (cholecalciferol), vitamin D precursors, metabolites and another analogous, and combinations thereof, as well as the various active and inactive forms of vitamin D. For example, and without limitation, vitamin $D_3$ may be provided in its unhydroxylated inactive form as cholecalciferol, or may be provided in its hydroxylated active form as calcitriol.

To state that a mammal has a "vitamin D deficiency," is "deficient in vitamin D," and so forth means generally, for example and without limitation, that such mammal has serum vitamin D levels that are less than optimal, and specifically includes both vitamin D deficiencies as well as vitamin D insufficiencies, as such terms are used in the medical arts.

By way of example and without limitation, according to current clinical guidelines (See, for example, Dawson-Hughes, B. "Treatment of vitamin D deficient states." *UpToDate*. Ed. Denise S. Basow. Waltham, Mass.: UpToDate in Waltham, 2009), vitamin D levels in humans are conventionally determined by measuring serum (25-hydroxy) vitamin D concentrations. As serum (25-hydroxy) vitamin D levels fall, calcium absorption decreases and parathyroid hormone ("PTH") concentrations rise. Therefore, the maximal suppression of PTH by vitamin D is one criterion by which an "optimal" serum (25-hydroxy) vitamin D concentration is defined. Although estimates vary, this concentration is generally understood to be in the 30 nanograms per milliliter (ng/mL) to 32 ng/mL range (Malabanan et al. (1998) *Lancet.* 351:805; Need et al. (2004) *J. Clin. Endocrinol. Metab.* 89:1646; Lamberg-Allardt et al. (2001) *Bone Miner. Res.* 16:2066; Hollis, B. W. (2005) *J. Nutr.* 135:317; Dawson-Hughes et al. (2005) *Osteoporos. Int.* 16:713). Higher serum (25-hydroxy) vitamin D concentrations (for example, 34 ng/mL versus 20 ng/mL) have been associated with greater calcium absorptive efficiency (Heaney et al. (2003) *J. Am. Coll. Nutr.* 22:142) and serum (25-hydroxy) vitamin D levels of 28 ng/mL to 40 ng/mL may lower fracture risk (Dawson-Hughes et al. (1997) *N. Engl. J. Med.* 337:670; Chapuy et al. (2002) *Osteoporos. Int.* 13:257; Trivedi et al. (2003) BMJ. 326:469). Although there is no consensus on the optimal serum (25-hydroxy) vitamin D concentration for skeletal health, it has been suggested that a minimum level of 30 ng/mL is necessary in adults (Dawson-Hughes et al. (2005); Vieth, R. (2006) *J. Nutr.* 136:1117; Vieth, R. (2006) *Prog. Biophys. Mol. Biol.* 92:26).

In view of this, current clinical guidelines generally define vitamin D insufficiency in adults as a serum (25-hydroxy) vitamin D concentration of 20 ng/mL to 30 ng/mL, and define vitamin D deficiency in adults as a serum (25-hydroxy) vitamin D concentration of less than 20 ng/mL. However, according to art-recognized usage, it is also understood that an individual with a serum (25-hydroxy) vitamin D concentration of less than 8 ng/mL may be considered vitamin D deficient, while an individual with a serum (25-hydroxy) vitamin D concentration of 8-20 ng/mL may be considered vitamin D insufficient. It is further understood that a serum (25-hydroxy) vitamin D concentration of 20-60 ng/mL may be referred to in the art to be "optimal," while a serum (25-hydroxy) vitamin D concentration of not less than 30 ng/mL may also be referred to in the art as "optimal."

Furthermore, although a serum (25-hydroxy) vitamin D concentration of 30 ng/mL may be considered optimal when measured using widely accepted radioimmunoassays or high performance liquid chromatography, it is understood in the art that significant variability may exist depending on the assay used (Binkley et al. (2004) *J. Clin. Endocrinol. Metab.* 89:3152). Moreover, although commercial assays generally measure total serum (25-hydroxy) vitamin D concentration, serum (25-hydroxy) vitamin $D_2$ and serum (25-hydroxy) vitamin $D_3$ values may be reported separately, in which case optimal serum concentration generally refers to the combined total.

It is further understood that a number of factors may impact what is considered "optimal" vitamin D levels for any individual, including for example and without limitation, geographic location, metabolic factors, sex, age, and other factors. An individual may also be considered to be deficient in vitamin D on a diagnostic basis, for example, where such individual exhibits symptoms or a phenotypic response known to be associated with a disease or disorder associated with low vitamin D levels. For example, even with the art-recognized definitions and clinical guidelines provided and discussed herein, it has been reported that current clinical guidelines do not account for ethnic differences and skeletal homeostasis (Harris, S. S. (2006) *J. Nutr.* 136:1126).

Accordingly, it is understood that the usage of "vitamin D deficiency," "vitamin D insufficiency," references to "optimal vitamin D levels," references to specific vitamin D levels, ranges, and so forth in the present invention is non-limiting and that such terms are to be construed broadly. Generally speaking, whether vitamin D supplementation is indicated is determined on a case-by-case basis. For example, although an individual with a serum (25-hydroxy) vitamin D concentration of at least 30 ng/mL may generally be considered within "optimal" range according to current clinical guidelines, a particular individual having such vitamin D levels (or having higher vitamin D levels) may nonetheless be deemed by a medical professional or otherwise to have sub-optimal vitamin D levels based on various criteria, for example if such individual is found to have low calcium absorption, exhibits symptoms of disorders and/or diseases associated with vitamin D deficiency and/or vitamin D insufficiency, and so forth.

As used herein, a "therapeutically effective amount" of a particular compound refers, for example and without limitation, to an amount of such compound that is effective to achieve a desired therapeutic result at a particular dosage, according to a particular dosing regimen, and over a particular period of time. The amount of a compound necessary to achieve a desired therapeutic result is influenced by, and will therefore vary based on, a number of factors, including for example and without limitation, the age, sex, and weight of the individual, factors that influence the metabolic rate of the individual, and any disorders and/or diseases of the individual (including the degree and severity thereof). Dosing regimens may be therefore be adjusted to achieve a desired therapeutic effect for a given individual. A "therapeutically effective amount" also refers to an amount at which negative factors, such as side effects and/or toxicity resulting from administration of the compound, are outweighed by the therapeutic benefits provided by administration of the compound.

As used herein, for example and without limitation, a "therapeutically effective amount" of vitamin D in the inventive sun-protecting formulations refers to an amount of vitamin D that is absorbed into the skin over a period of time to cause a measurable increase in serum (25-hydroxy) vitamin D levels, which may be determined using conventional pharmacokinetic analysis and techniques known to those of skill in the art. As the inventive formulations include sun-protecting components, in various embodiments achieving a therapeutically effective amount of vitamin D will take into account various factors attendant to sun-protecting formulations, for example and without limitation, that such formulations may be exposed to water (including alkaline salt water), may be partially removed by "towel drying" after a period of time, and so forth, and therefore in such embodiments such factors may be taken into account to ensure that a therapeutically effective amount of vitamin D is administered to the individual, for example and without limitation, the concentration of vitamin D, the delivery mechanism, and the inclusion of specific ingredients such as stabilizers, penetration enhancers, waterproofing agents, and so forth. In certain embodiments, it may be intended that the inventive formulations be re-applied after a certain period of time for particular therapeutic purposes, which will be taken into account in determining the concentration of vitamin D and ingredients present in such formulations.

By way of further example and without limitation, a "therapeutically effective amount" of vitamin D present in the inventive sun-protecting formulations is one in which improvement is realized with respect to one or more disorders and/or disease states associated with vitamin D deficiency and/or vitamin D insufficiency in an individual. Such disorders and disease states include, for example and without limitation, all known disease states and disorders associated with vitamin D deficiency and vitamin D insufficiency, including those discussed herein, regardless of whether such vitamin D deficiency and/or vitamin D insufficiency is due to environmental, dietary and/or physiological factors.

By way of further example and without limitation, a "therapeutically effective amount" of vitamin D present in the inventive sun-protecting formulations is one in which a specific amount of vitamin D is administered systemically to an individual, in order to replace vitamin D that is not made naturally due to the sun-protecting component(s) in of the formulations. It is understood that those of ordinary skill in the art will, based on the teachings herein, be capable of empirically determining the therapeutically effective amount of vitamin D needed in specific embodiments of the present inventive to achieve a particular therapeutic benefit, without the need for undue experimentation (as well as, in certain embodiments, determining therapeutically effective amounts of other agents that may be included in the inventive formulations in combination with vitamin D, to provide various therapeutic benefits).

The inventive formulations may, in various exemplary, non-limiting embodiments, be provided in forms suitable for topical administration and that result in the transdermal delivery of a therapeutically effective amount of vitamin D, for example and without limitation the inventive formulations may be provided as creams, gels, liquids, lotions, solutions, sprays, emulsions, aerosols, and combinations thereof, and may provide multi-lamellar vesicles, liposomes, nanospheres, microsponges, or combinations thereof. In certain exemplary, non-limiting embodiments, the active agents, including vitamin D, may be encapsulated (including microencapsulated) in the inventive formulations, for example, to be released when the encapsulation is ruptured under pressure, for time-release of the agent, and so forth. Suitable encapsulating materials and techniques, including those which release the encapsulated agent over time, are known in the art.

Other conventional cosmetic and/or pharmaceutical agents may be provided in the inventive formulations, so long as they are physiologically acceptable and suitable for use in combination with the one or more sun-protecting agents and therapeutically effective amount of vitamin D provided in the formulations.

For example, the inventive formulations may include physiologically compatible vehicles and excipients, such as water, alcohol, and derivatives, combinations, and mixtures thereof. In certain desired embodiments, the inventive formulations include oil-free vehicles.

For example, the inventive formulations may include emollients, such as fatty esters, fatty alcohols, mineral oils, polyether siloxane copolymers, polypropylene glycol (PPG)-15 stearyl ether, PPG-10 acetyl ether, steareth-10, oleth-8, PPG-4 lauryl ether, vitamin E acetate, PEG-7 glyceryl cocoate, lanolin, cetyl alcohol, octyl hydroxystearate, dimethicone, cetyl alcohol, octyl hydroxystearate, dimethicone, and derivatives, combinations, and mixtures thereof.

For example, the inventive formulations may include skin conditioning agents, such as colloidal oatmeal, olive leaf, sulfonated shale oil, elubiol, 6-(1-piperidinyl)-2,4-pyrimidinediamine-3-oxide, finasteride, ketoconazole, zinc pyrithione, coal tar, benzoyl peroxide, selenium sulfide, hydrocortisone, pramoxine hydrochloride, tricetylammonium chloride, polyquaternium 10, panthenol, panthenol triacetate, vitamin B, vitamin C, vitamin D, vitamin E, vitamin K, keratin, lysine, arginine, hydrolyzed wheat proteins, hydrolyzed silk proteins, octyl methoxycinnamate, oxybenzone, minoxidil, titanium dioxide, zinc dioxide, erthromycin, tretinoin, and derivatives, combinations, and mixtures thereof.

For example, the inventive formulations may include pH stabilizing agent(s), such as butylated hydroxy toluene (BHT), ethylene diamine tetra acetic acid (EDTA), triethanolamine (TEA), gylcerin, propylene glycol, and derivatives, combinations, and mixtures thereof.

For example, the inventive formulations may include humectants, such as polyhydric alcohols, including glycerol/glycerin, polyalkylene glycols, alkylene polyols, including butylene glycol, propylene glycol, dipropylene glycol, polypropylene glycol, and polyethylene glycol, sorbitol, hydroxypropyl sorbitol, hexylene glycol, 1,3-dibutylene glycol, 1,2,6,-hexanetriol, ethoxylated glycerol, propoxylated glycerol, and derivatives, combinations, and mixtures thereof.

For example, the inventive formulations may include buffering agents, such as citric acid, sodium citrate, and derivatives, combinations, and mixtures thereof.

For example, the inventive formulations may include viscosity adjusting agents, such as carbomer gelling agents, gum derivatives, and derivatives, combinations, and mixtures thereof.

For example, the inventive formulations may include preservatives, such as methylparaben, ethylparaben, butylparaben, propylparaben, phenoxyethanol, and derivatives, combinations, and mixtures thereof.

For example, the inventive formulations may include chelating agents, such as ethylenediamine tetra acetic acid (EDTA), dihydroxyethyl glycine, tartaric acid, and derivatives, combinations, and mixtures thereof.

For example, the inventive formulations may include emulsifying agents, such as polysorbitate 80, glyceryl distearate, POE 10 stearyl ether, ceateareth 20, stearyl alcohol, cetareth 20, cetearyl alcohol, and derivatives, combinations, and mixtures thereof. In certain desired embodiments, the inventive formulations include oil-free emulsifying agents.

For example, the inventive formulations may include conditioning agents, such as octyl hydroxystearate; emollients, such as cholesterol NF, petrolatum, mineral oils and esters, including isopropyl myristate, isopropyl palmitate, 1-decene polymer (hydrogenated), and $C_{12}$-$C_{15}$ alcohol benzoates, and derivatives, combinations, and mixtures thereof.

For example, the inventive formulations may include thickening agents, such as polyacrylamide, $C_{13}$-$C_{14}$ isoparafin, laureth-7, and derivatives, combinations, and mixtures thereof.

For example, the inventive formulations may include antioxidants, such as ascorbic acid, ascorbyl palmitate, BHT, tocopheryl acetate, butylated hydroanisole (BHA), phenyl-α-naphthylamine, hydroquinone, propyl gallate, nordihydroquiaretic acid, *Garcinia Mangostana* (Mangosteen) Peel Extract, *Camellia Sinensis* (Green and White Tea) Leaf Extract, *Punica Granatum* (Pomegranate) Extract, and derivatives, combinations, and mixtures thereof.

In certain desired embodiments, the inventive formulations include, or are provided in combination with a separate formulation that includes, the antioxidants *Garcinia Mangostana* (Mangosteen) Peel Extract, *Camellia Sinensis* (Green and White Tea) Leaf Extract, and *Punica Granatum* (Pomegranate) Extract together in combination.

For example, the inventive formulations may include UV stabilizers.

For example, the inventive formulations may include UV radiation absorbers (sunscreen filters).

For example, the inventive formulations may include fragrances, such as eucalyptus oil, camphor synthetic, peppermint oil, clove oil, lavender, chamomile, and derivatives, combinations, and mixtures thereof.

For example, the inventive formulations may include colorants.

The inventive formulations may also including mixtures and combinations and any of the above.

The inventive formulations may also include one or more active agents in addition to the therapeutically effective dose of vitamin D, for example and without limitation, agents for the prevention and treatment of one or more disorders and/or disease states associated with vitamin D deficiency and/or vitamin D insufficiency.

In certain exemplary, non-limiting embodiments, the inventive formulations have an SPF of about 2 to about 95, and in certain exemplary, non-limiting embodiments have an SPF of greater than 95. It is understood that the inventive formulations are not limited to any particular SPF or SPF range, and formulations having any SPF are contemplated in the present invention.

It is understood that vitamin D may be present in the inventive formulations in any suitable amount. For example, in certain exemplary, non-limiting embodiments, vitamin D is present in the inventive formulations at a concentration that results in administration of vitamin D to the skin at a concentration of about of about 0.1 International Units per square centimeter ($IU/cm^2$) to about 1000 $IU/cm^2$, and in certain desired, non-limiting embodiments is present in the inventive formulations at a concentration that results in administration of vitamin D to the skin at a concentration of about 0.1 $IU/cm^2$ to about 10.0 $IU/cm^2$.

As discussed herein, when topically administered, the inventive formulations result in an increase in vitamin D levels, and such increase is not limited to any particular vitamin D level or range of vitamin D levels. In certain desired, non-limiting embodiments, when topically administered, the inventive formulations result in serum vitamin D levels of about 20 ng/mL to about 100 ng/mL; and in certain desired, non-limiting embodiments, when topically administered, the inventive formulations result in serum vitamin D levels of about 30 ng/mL to about 60 ng/mL The discussion herein and the following Examples set forth and illustrate various exemplary embodiments of the present invention, which are understood to be illustrative and non-limiting.

Example 1

Sun-Protecting Formulations for Maintaining Optimal Vitamin D Levels

A sun-protecting formulation is prepared according to art-recognized techniques to have at least one sun-protecting agent in combination with an amount of vitamin D therapeutically effective for maintaining optimal vitamin D levels despite reduced sun exposure to the skin.

The included sun-protecting agent(s) result in a "sunscreen formulation" having a relatively high SPF, which, when applied topically, permits an individual to engage in outdoor activity while reducing or eliminating skin exposure to harmful UVA and/or UVB rays. This reduced skin exposure, however, reduces or prevents, for a period of time, the natural production of vitamin D, and thus these inventive formulations are provided with vitamin D in therapeutically effective amounts to compensate for the effects of these formulations on natural vitamin D production, such that optimal vitamin D levels are maintained in the individual.

Various formulations according to this Example may be provided in which the specific sun-protecting agent(s), concentration of vitamin D, and other ingredients, are selected for each formulation based on the specific intended use of the resulting formulation, including the environmental and other conditions in which the formulation is intended to be used, whether the formulation is intended to be re-applied after particular activities and/or after specific periods of time, and specific characteristics of the individual that may impact the transdermal delivery of vitamin D in that individual.

Accordingly, these inventive formulations may be provided for use by a number of individuals engaged in varied activities and using these inventive formulations under varied conditions, while in all cases protecting such individuals against the harmful effects of UVA and/or UBV rays while maintaining optimal vitamin D levels in such individuals.

Example 2

Sun-Protecting Formulations for Treating Vitamin D Deficiency and/or Vitamin D Insufficiency and for Preventing Disorders and Disease States Associated Therewith A sun-protecting formulation is prepared according to art-recognized techniques to have at least one sun-protecting agent in combination with an amount of vitamin D therapeutically effective to treat a vitamin D deficient or vitamin D insufficient individual, thereby resulting in increased vitamin D levels in such individual while eliminating or reducing the need for sun exposure to the skin, which may thereby prevent the onset of various disease states associated with low vitamin D levels.

In such formulations, the choice of sun-protecting agent(s) will depend on a number of factors, including the desired SPF of the resulting formulation. For example, a lower SPF rating may be desired by vitamin D deficient or vitamin D insufficient individuals who wish to minimize, but not completely eliminate, UVA and/or UVB exposure, while vitamin D deficient or vitamin D insufficient individuals having specific photosensitivities, including, for example, photosensitivities resulting from certain disorders and/or disease states (including, for example, certain disorders and/or disease states specifically associated with vitamin D deficiency and/or vitamin D insufficiency), may require a formulation having a higher SPF to completely prevent sun exposure to the skin. In all cases, however, the inventive formulation provides a therapeutically effective amount of vitamin D that is administered transdermally to increase vitamin D levels, desirably to optimal vitamin D levels, while permitting the individual to engage in outdoor activity.

As with the inventive formulations discussed in Example 1, these inventive treatment formulations may be provided in which the specific sun-protecting agent(s), concentration of vitamin D, and other ingredients, are selected for each inventive formulation based on the specific intended use of the resulting inventive formulation, including the environmental and other conditions in which the inventive formulation is intended to be used, and whether the inventive formulation is intended to be re-applied after particular activities and/or after specific periods of time, and also taking into account specific characteristics of the individual for whom it is intended that may impact transdermal vitamin D delivery in such individual.

Accordingly, these inventive treatment formulations may be provided for use by a number of individuals engaged in varied activities and using these inventive treatment formulations under varied conditions, while in all cases protecting such individuals against the harmful effects of UVA and/or UBV rays while increasing vitamin D levels in such individuals.

Example 3

Sun-Protecting Formulations for Treating Disorders and/or Disease States Associated with Vitamin D Deficiency and/or Vitamin D Insufficiency A sun-protecting formulation is prepared according to art-recognized techniques to have at least one sun-protecting agent in combination with an amount of vitamin D therapeutically effective to treat a disorder and/or disease associated with vitamin D deficiency and/or vitamin D insufficiency. As discussed herein, such disorders and/or diseases which may be treated using the inventive formulations include, for example and without limitation, disorders and diseases associated with low calcium uptake; bone-related disorders and diseases including osteopenia, osteomalacia, osteoporosis, and rickets; vascular disorders and diseases including coronary artery disease, high blood pressure, and peripheral artery disease; autoimmune disorders and diseases including multiple sclerosis, fibromyalgia, rheumatoid arthritis, Grave's disease, and lupus; tuberculosis; periodontal disorders and diseases; chronic pain; seasonal affective disorder; cognitive impairment; depression; type I diabetes; chronic renal disease; hypoparathyroid; Parkinson's disease, and certain types of cancers, including breast cancer, prostate cancer, colon cancer, and skin cancer.

As with the formulations discussed above, in these inventive treatment formulations, the choice of sun-protecting agent(s) will depend on a number of factors, including the desired SPF of the resulting inventive formulation. For example, a lower SPF rating may be desired by individuals who wish to minimize, but not completely eliminate, UVA and/or UVB exposure, while individuals having specific photosensitivities, and in particular individuals having sun-sensitivity as a result of certain disorders and/or diseases, for example immune disorders, may require a formulation having a higher SPF to completely prevent sun exposure to the skin.

In all cases, however, these inventive formulations provide a therapeutically effective amount of vitamin D that is administered transdermally to increase vitamin D levels in an individual, desirably to optimal vitamin D levels, while permitting such individual to engage in outdoor activity.

As with the inventive formulations discussed above, these inventive treatment formulations may be provided in which the specific sun-protecting agent(s), concentration of vitamin D, and other ingredients, are selected for each inventive formulation based on the specific intended use of the resulting formulation, including the environmental and other conditions in which the inventive formulation is intended to be used, and whether the inventive formulation is intended to be re-applied after particular activities and/or after specific periods of time, and also taking into account specific characteristics of the individual for whom it is intended that may impact transdermal vitamin D delivery in such individual.

Accordingly, these inventive formulations may be provided for use by a number of individuals engaged in varied activities and using these inventive treatment formulations under varied conditions, while in all cases protecting such individuals against the harmful effects of UVA and UBV rays while administering vitamin D in a therapeutically effective amount to treat disorders and/or diseases in such individuals.

Example 4

Formulations

From the teachings provided herein, those of skill in the art will be able to make the inventive formulations having one or more sun-protecting agents and a therapeutically effective amount of vitamin D, and test the safety and efficacy of such inventive formulations in established animal models (for example and without limitation, animal models suited for transdermal drug delivery) and using conventional pharmacokinetic analysis and techniques, as well as prepare such inventive formulations using ingredients to render them suitable for use by particular individuals, for use during particular activities, and/or for use when exposed to particular environmental conditions.

It is understood that sunscreen formulations are conventionally tested at a skin concentration of about 2 $mg/cm^2$ and therefore it is contemplated that the formulations within the present invention may be tested at or about such concentration, but it is further understood that the safety and efficacy of the formulations within the scope of the present invention may be determined on the basis of any skin concentration at which it is intended to be applied, and that in certain embodiments specific instructions may be provided, and/or the formulation itself may be provided in a particular form, to ensure that a the formulation is topically administered at the intended concentration (for example and without limitation, in certain embodiments a formulation of the present invention may be provided in metered doses, such as for use on certain parts of the body).

Once given the above disclosure, many other features, modifications, and improvements will become apparent to the skilled artisan. Such features, modifications, and improvements are therefore considered to be part of this invention, without limitation imposed by the example embodiments described herein. Moreover, any word, term, phrase, feature, example, embodiment, or part or combination thereof, as used to describe or exemplify embodiments herein, unless unequivocally set forth as expressly uniquely defined or otherwise unequivocally set forth as limiting, is not intended to impart a narrowing scope to the invention in contravention of the ordinary meaning of the claim terms by which the scope of the patent property rights shall otherwise be determined. All references discussed and disclosed herein are hereby incorporated by reference in their entirety.

What is claimed is:

1. A therapeutic sun-protecting composition, comprising: (a) at least one sun-protecting agent; (b) at least one physiologic biological vitamin D compound said physiologic biological vitamin D compound being present in a therapeutically effective amount such that, upon topical administration to a mammal, said physiologic biological vitamin D compound is absorbed through the skin of said mammal and causes a measurable increase in said mammal's serum physiologic biological vitamin D levels in the absence of an alcohol carrier; and (c) a pharmaceutical carrier effective for topical administration of said at least one sun-protecting agent and said at least one physiologic biological vitamin D compound, wherein said physiologic biological vitamin D compound is separated from said sun-protecting agent within said therapeutic sun-protecting composition.

2. A therapeutic sun-protecting composition according to claim 1, wherein said at least one physiologic biological vitamin D compound is present in an amount to compensate for a reduction in said mammal's vitamin D production.

3. A therapeutic sun-protecting composition according to claim 1, wherein said mammal has a vitamin D deficiency or has a vitamin D insufficiency.

4. A therapeutic sun-protecting composition according to claim 3, wherein said mammal has a serum (25-hydroxy) vitamin D concentration of less than about 20 ng/mL; of less than about 30 ng/mL; of less than about 40 ng/mL; or of less than about 50 ng/mL.

5. A therapeutic sun-protecting composition according to claim 1, wherein administration of said at least one physiologic biological vitamin D compound to said mammal results in a serum (25-hydroxy) vitamin D concentration in said mammal in a range of about 20 ng/mL to about 100 ng/mL.

6. A therapeutic sun-protecting composition according to claim 1, wherein said at least one physiologic biological vitamin D compound is present in said therapeutic sun-protecting composition at a concentration that results in administration of said at least one physiologic biological vitamin D compound to the skin of said mammal at a concentration of about 0.1 IU/cm$^2$ to about 1000 IU/cm$^2$ or at a concentration of about 0.1 IU/cm$^2$ to about 10.0 IU/cm$^2$.

7. A therapeutic sun-protecting composition according to claim 1, wherein said at least one sun-protecting agent is selected from the group consisting of aminobenzoic acid, avobenzone, benzophenone, benzophenone-3, cinnamates, cinoxate, dioxybenzone, ecamsule, ensulizole, ethylhexyl p-methoxycinnamate, homosalate, menthyl anthranilate, meradimate, octinoxate, octisalate, octocrylene, octyl dimethyl paba, octyl methoxycinnamate (OMC), octyl salicytate (OCS), oxybenzone, padimate-O, para-aminobenzoic acid (PABA), Parsol® 1789, salicylates, sulisobenzone, sulisobenzone, titanium dioxide, trolamine salicylate, and zinc oxide.

8. A therapeutic sun-protecting composition according to claim 1, wherein said at least one physiologic biological vitamin D compound is selected from the group consisting of vitamin D2 (ergocalciferol), vitamin D3 (cholecalciferol), active forms, and metabolites thereof.

9. A therapeutic sun-protecting composition according to claim 1, wherein said at least one sun-protecting agent, said at least one physiologic biological vitamin D compound, and said pharmaceutical carrier are provided in combination in the form of a cream, gel, liquid, lotion, solution, spray, emulsion, aerosol, or a combination thereof.

10. A therapeutic sun-protecting composition according to claim 1, wherein said pharmaceutically effective carrier for the sun-protecting agent is selected from the group consisting of water, alcohol, other oil-free carriers, or mixtures thereof.

11. A therapeutic sun-protecting composition according to claim 1, further comprising one or more of the following: at least one emollient; at least one skin condition agent; at least one humectant; at least one emulsifying agent; at least one conditioning agent; at least one stabilizing agent; at least one thickening agent; at least one antioxidant; at least one UV stabilizer; and at least one UV radiation absorber.

12. A therapeutic sun-protecting composition according to claim 11, wherein (a) said at least one emollient is selected from the group consisting of fatty esters, fatty alcohols, mineral oils, polyether siloxane copolymers, polypropylene glycol ("PPG")-15 stearyl ether, PPG-10 acetyl ether, steareth-10, oleth-8, PPG-4 lauryl ether, vitamin E acetate, PEG-7 glyceryl cocoate, lanolin, cetyl alcohol, octyl hydroxystearate, dimethicone, cetyl alcohol, octyl hydroxystearate, dimethicone, derivatives, combinations, and mixtures thereof; (b) said at least one skin condition agent is selected from the group consisting of colloidal oatmeal, olive leaf, sulfonated shale oil, elubiol, 6-(1-piperidinyl)-2,4-pyrimidinediamine-3-oxide finasteride, ketoconazole, zinc pyrithione, coal tar, benzoyl peroxide, selenium sulfide, hydrocortisone, pramoxine hydrochloride, tricetylammonium chloride, polyquaternium 10, panthenol, panthenol triacetate, vitamin B, vitamin C, vitamin D, vitamin E, vitamin K, keratin, lysine, arginine, hydrolyzed wheat proteins, hydrolyzed silk proteins, octyl methoxycinnamate, oxybenzone, minoxidil, titanium dioxide, zinc dioxide, erthromycin, tretinoin, derivatives, combinations, and mixtures thereof; (c) said least one humectant is a polyhydric alcohol selected from the group consisting of glycerol/glycerin, polyalkylene glycols, alkylene polyols, including butylene glycol, propylene glycol, dipropylene glycol, polypropylene glycol, and polyethylene glycol, sorbitol, hydroxypropyl sorbitol, hexylene glycol, 1,3-dibutylene glycol, 1,2,6-hexanetriol, ethoxylated glycerol, propoxylated glycerol, derivatives, combinations, and mixtures thereof; (d) said at least one emulsifying agent is selected from the group consisting of polysorbitate 80, glyceryl distearate, POE 10 stearyl ether, ceateareth 20, stearyl alcohol, ceteareth 20, cetearyl alcohol, POE 2 stearyl ether, other oil-free emulsifying agents, derivatives, combinations, and mixtures thereof; (e) said at least one conditioning agent is selected from the group consisting of octyl hydroxystearate; emollients, such as cholesterol NF, petrolatum, mineral oils and esters, including isopropyl myristate, isopropyl palmitate, 1-decene polymer (hydrogenated), and $C_{12}$-$C_{15}$ alcohol benzoates, tocopherol, tocotrienol, and derivatives, combinations, and mixtures thereof; (f) said at least one stabilizing agent is selected from the group consisting of butylated hydroxy toluene (BHT), ethylene diamine tetra acetic acid (EDTA), triethanolamine (TEA), gylcerin, propylene glycol, derivatives, combinations, and mixtures thereof; (g) said at least one thickening agent is selected from the group consisting of polyacrylamide, $C_{13}$-$C_{14}$ isoparafin, laureth-7, and derivatives, combinations, and mixtures thereof; and (h) said at least one antioxidant is selected from the group consisting of ascorbic acid, ascorbyl palmitate, BHT, tocopheryl acetate, butylated hydroanisole (BHA), phenyl-α-naphthylamine, hydroquinone, propyl gallate, nordihydroquiaretic acid, *Garcinia Mangostana* (Mangosteen) Peel Extract, *Camellia Sinensis* (Green and White Tea) Leaf Extract, *Punica Granatum* (Pomegranate) Extract, tocopherol, tocotrienol, and derivatives, combinations, and mixtures thereof.

13. A method of preventing disorders and diseases associated with vitamin D deficiency or vitamin D insufficiency, comprising topically administering to a mammal a therapeutic sun-protecting composition according to claim 1.

14. A method of preventing disorders and diseases associated with vitamin D deficiency or vitamin D insufficiency according to claim 13, wherein said therapeutic sun-protecting composition is topically administered to said mammal in a single application, or is topically administered to said mammal in multiple applications.

15. A method of treating disorders and diseases associated with vitamin D deficiency or vitamin D insufficiency, comprising topically administering to a mammal having at least one disorder or disease associated with vitamin D deficiency a therapeutic sun-protecting composition according to claim 1.

16. A method of treating disorders and diseases associated with vitamin D deficiency or vitamin D insufficiency according to claim 15, wherein said therapeutic sun-protecting composition is topically administered to said mammal in a single application, or is topically administered to said mammal in multiple applications.

17. A therapeutic sun-protecting composition according to claim 1, wherein said separation of said physiologic biological vitamin D compound from said sun-protecting agent results from encapsulation of said physiologic biological vitamin D compound within said therapeutic sun-protecting composition.

18. A therapeutic sun-protecting composition according to claim 1, wherein said separation of said physiologic biological vitamin D compound from said sun-protecting agent results from a difference in the solubility of said physiologic biological vitamin D compound in said pharmaceutical carrier and the solubility of said sun-protecting agent in said pharmaceutical carrier.

19. A therapeutic sun-protecting composition according to claim 1, wherein said separation of said physiologic biological vitamin D compound from said sun-protecting agent results from said physiologic biological vitamin D compound and said sun-protecting agent being in separate phases within said therapeutic sun-protecting composition.

20. A therapeutic sun-protecting composition according to claim 19, wherein said separate phases include a relatively lipophilic phase and a relatively hydrophilic phase.

21. A therapeutic sun-protecting composition according to claim 1, wherein said separation of said physiologic biological vitamin D compound from said sun-protecting agent results from chemical binding of said physiologic biological vitamin D compound and/or said sun-protecting agent to said pharmaceutical carrier.

22. A therapeutic sun-protecting composition according to claim 1, further comprising a second pharmaceutical carrier effective for topical administration of the other of said at least one sun-protecting agent and said at least one physiologic biological vitamin D compound that is delivered by said pharmaceutical carrier effective for topical administration of said at least one sun-protecting agent and said at least one physiologic biological vitamin D compound.

23. A therapeutic sun-protecting formulation prepared by a process comprising the steps of: (a) providing a therapeutically effective amount of a physiologic biological vitamin D compound: (b) providing a pharmaceutical carrier effective for topical administration of said physiologic biological vitamin D compound, said pharmaceutical carrier being capable of delivering said physiologic biological vitamin D compound to a mammal to cause a measurable increase in said mammal's serum vitamin D levels while decreasing the exposure of said mammal's skin to UV radiation, wherein said pharmaceutical carrier is capable of delivering said physiologic biological vitamin D compound to cause a measurable increase in said mammal's serum vitamin D levels in the absence of alcohol; and (c) mixing said physiologic biological vitamin D compound and said pharmaceutical carrier.

24. A therapeutic sun-protecting composition, comprising: (a) at least one sun-protecting agent capable of absorbing ultraviolet radiation; (b) at least one therapeutic physiologic biological vitamin D compound; and (c) a pharmaceutical carrier, wherein, upon topical administration of said therapeutic sun-protecting composition to a mammal, said pharmaceutical carrier simultaneously delivers (i) said therapeutic physiologic biological vitamin D compound through the skin and into the bloodstream of said mammal to cause a measurable increase in said mammal's serum vitamin D levels in the absence of an alcohol carrier; and (ii) said sun-protecting agent to the surface of the skin of said mammal.

* * * * *